US010982290B2

(12) United States Patent
Horton et al.

(10) Patent No.: US 10,982,290 B2
(45) Date of Patent: Apr. 20, 2021

(54) SCREENING AND MONITORING THE PROGRESSION OF TYPE 2 DIABETES BY THE MOLECULAR IDENTIFICATION OF HUMAN GUT FLORA USING FTA AS A FAECAL COLLECTION DEVICE

(71) Applicant: Global Life Sciences Solutions Operations UK Ltd, Sheffield (GB)

(72) Inventors: Jeffrey Kenneth Horton, Cardiff (GB); Peter James Tatnell, Cardiff (GB); Matthew Sam Morrison, Buckinghamshire (GB); Alan Stuart Pierce, Cardiff (GB)

(73) Assignee: Global Life Sciences Solutions Operations UK Ltd, Sheffield (GB)

( * ) Notice: Subject to any disclaimer, the term of this patent is extended or adjusted under 35 U.S.C. 154(b) by 36 days.

(21) Appl. No.: 15/326,382

(22) PCT Filed: Jul. 23, 2015

(86) PCT No.: PCT/US2015/041779
§ 371 (c)(1),
(2) Date: Jan. 13, 2017

(87) PCT Pub. No.: WO2016/014822
PCT Pub. Date: Jan. 28, 2016

(65) Prior Publication Data
US 2017/0211130 A1 Jul. 27, 2017

Related U.S. Application Data

(63) Continuation-in-part of application No. PCT/US2015/041779, filed on Jul. 23, 2015.

(60) Provisional application No. 62/029,155, filed on Jul. 25, 2014.

(51) Int. Cl.
| | | |
|---|---|---|
| *C12Q 1/68* | (2018.01) | |
| *C12Q 1/00* | (2006.01) | |
| *C12Q 1/10* | (2006.01) | |
| *C12Q 1/689* | (2018.01) | |
| *C12Q 1/6883* | (2018.01) | |
| *C12Q 1/06* | (2006.01) | |
| *A61K 38/00* | (2006.01) | |
| *C12Q 1/6827* | (2018.01) | |

(52) U.S. Cl.
CPC .......... *C12Q 1/689* (2013.01); *C12Q 1/6883* (2013.01); *A61K 38/00* (2013.01); *C12Q 1/06* (2013.01); *C12Q 1/6827* (2013.01); *C12Q 2600/118* (2013.01); *C12Q 2600/158* (2013.01); *C12Q 2600/16* (2013.01)

(58) Field of Classification Search
CPC . C12Q 1/689; C12Q 1/6883; C12Q 2600/118
See application file for complete search history.

(56) References Cited

U.S. PATENT DOCUMENTS

| | | | | |
|---|---|---|---|---|
| 2002/0086289 A1* | 7/2002 | Straus | .................. | C12Q 1/6827 435/6.18 |
| 2009/0325263 A1* | 12/2009 | Ponaka | ..................... | C12N 1/04 435/178 |
| 2010/0015628 A1* | 1/2010 | Farchaus | .............. | C12Q 1/6806 435/6.11 |
| 2011/0111503 A1 | 5/2011 | Siedel et al. | | |
| 2013/0040828 A1 | 2/2013 | Xue et al. | | |
| 2013/0030339 A1 | 11/2013 | Vebo et al. | | |

FOREIGN PATENT DOCUMENTS

| | | | |
|---|---|---|---|
| EP | 2 338 989 A1 | | 6/2011 |
| WO | WO 2010/066908 | * | 6/2010 |
| WO | 2012/080754 A2 | | 6/2012 |
| WO | 2013/153359 A1 | | 10/2013 |

OTHER PUBLICATIONS

Cavallini et al., Journal of Microbiological Methods, 2000; 39: 265-270 (Year: 2000).*
Wang et al., Appl Microbiol Biotechnol, 2010, 88:1333-1342 (Year: 2010).*
Kim et al., Applied and environmental microbiology, (Nov. 2011) vol. 77, No. 22, pp. 8062-8070. (Year: 2011).*
Nechvatal et al., Journal of Microbiological Methods, 2008; 72: 124-132 (Year: 2008).*
De Vega et al., PNAS, 2010; 107(38):16506-16511 (Year: 2010).*
Yadav et al., Biomedical Engineering and Computational Biology, 2013; 5: 43-49 (Year: 2013).*
Matsuki et al., Applied and Environmental Microbiology, 2004; 70(12): 7220-77228 (Year: 2013).*
International Search Report and Written Opinion regarding International Application No. PCT/US2015/41779, dated Oct. 28, 2015, 8 pages.
European Search Report for EP Application No. 15824750.2 dated Nov. 14, 2017 (8 pages).
Larsen et al., "Gut Microbiota in Human Adults with Type 2 Diabetes Differs from Non-Diabetic Adults," PloS One, 2010, 5(2):e9085 (10 pages).

(Continued)

*Primary Examiner* — Gary B Nickol
*Assistant Examiner* — Lakia J Jackson-Tongue
(74) *Attorney, Agent, or Firm* — Eversheds Sutherland (US) LLP

(57) ABSTRACT

Disclosed is a method for detecting and quantifying gut flora derived from human faeces, comprising acquiring a solid support containing human faeces; optionally amplifying nucleic acid from the human faeces; and detecting and quantifying the presence of gut flora of interest. Also disclosed is a method for assessing whether a person has type-2 diabetes as well as a kit for detecting and quantifying gut flora from human faeces, comprising a solid support for collecting human faeces; and primer pairs for amplifying 16S rRNA sequence from bacteria of interest.

8 Claims, No Drawings

Specification includes a Sequence Listing.

(56) References Cited

OTHER PUBLICATIONS

Layton et al., "Development of Bacteroids 16S rRNA Gene TaqMan-Based Real-Time PCR Assays for Estimation of Total, Human, and Bovine Fecal Pollution in Water," Applied and Environmental Microbiology, 2006, 72(6):4214-4224.
Paliy et al., "High-Throughput Quantitative Analysis of the Human Intestinal Microbiota with a Phylogenetic Microarray," Applied and Environmental Microbioloty, 2009, 75(11):3572-3579.
European Office Action for EP Application No. 15824750.2 dated May 9, 2019 (4 pages).
Nechvatal et al., "Fecal Collection, Ambient Preservation, and DNA Extraction for PCR Amplification of Bacterial and Human Markers from Human Feces," Journal of Microbiological Methods, 2008, 72:124-132.
European Office Action for EP Application No. 15824750.2 dated May 18, 2020 (5 pages).
Chu et al., "Detection of Cyclospora Cayetanensis in Animal Fecal Isolates from Nepal using an FTA Filter-Base Polymerase Chain Reaction Method," Am. J. Trop. Med. Hyg., 2004, 71(4):373-379.
Subrungruang et al., "Evaluation of DNA Extraction and PCR Methods for Detection of Enterocytozoon bienuesi in Stool Specimens," Journal of Clinical Microbiology, 2004, 3490-3494.

\* cited by examiner

SCREENING AND MONITORING THE PROGRESSION OF TYPE 2 DIABETES BY THE MOLECULAR IDENTIFICATION OF HUMAN GUT FLORA USING FTA AS A FAECAL COLLECTION DEVICE

CROSS-REFERENCE TO RELATED APPLICATIONS

This application is a filing under 35 U.S.C. 371 of international application number PCT/US2015/041779, filed Jul. 23, 2015, which claims priority to U.S. application No. 62/029,155, filed Jul. 25, 2014, the entire disclosures of each of which are hereby incorporated by reference.

FIELD OF THE INVENTION

The present invention relates to methods and kits for detecting gut flora derived from human faeces. More specifically, it relates to methods and kits for the screening and monitoring of certain disease or condition by molecular identification of gut flora using faeces collected using a solid support.

BACKGROUND OF THE INVENTION

The incidence of type 2 diabetes mellitus is increasing worldwide. Type 2 diabetes results from the interaction between a genetic predisposition and behavioural and environmental risk factors. Although the genetic basis of type 2 diabetes has yet to be identified, there is strong evidence that modifiable risk factors such as obesity and physical inactivity are the main non-genetic determinants of the disease.

Type 2 diabetes mellitus consists of an array of dysfunctions characterized by hyperglycemia and resulting from the combination of resistance to insulin action, inadequate insulin secretion, and excessive or inappropriate glucagon secretion. Poorly controlled type 2 diabetes is associated with an array of micro- and macro-vascular, and neuropathic complications. Micro-vascular complications of diabetes include serious retinal, renal, and possibly neuropathic disease. Macro-vascular complications include coronary artery and peripheral vascular disease. Diabetic neuropathy affects autonomic and peripheral nerves. Thus control of type 2 (non-insulin dependent) diabetes such as non-insulin-dependent diabetes mellitus (NIDDM) and Type 1 (insulin dependent) disease has serious implications for patient morbidity and clinical management.

Diabetes mellitus (Type 1 & 2) is characterized by recurrent or persistent hyperglycemia, and is diagnosed by demonstrating any one of the following:

Fasting plasma glucose level≥7.0 mmol/l (126 mg/dl)
Plasma glucose≥11.1 mmol/l (200 mg/dL) two hours after a 75 g oral glucose load as in a glucose tolerance test
Symptoms of hyperglycemia and casual plasma glucose≥11.1 mmol/l (200 mg/dl)
Glycated hemoglobin (Hb A1C)≥6.5%

Impaired glucose tolerance is an intermediate category between normal glucose tolerance and overt diabetes, and it can be identified by an oral glucose tolerance test and is a good initial diagnostic tool for the onset of Type 2 diabetes. A glucose tolerance test is a medical investigation in which glucose is given and blood samples taken afterward to determine how quickly it is cleared from the blood. The test is usually used to test for diabetes and insulin resistance. This test, however, gives very little information on the progression of the disease. Type 2 diabetes is a progressive disease characterized by worsening of multiple abnormalities and loss of glycaemic control over time. An increasing need for glucose-lowering treatments is emphasised by the almost inevitable failure of monotherapy and occurrence of weight gain. Longer survival times and development of type 2 diabetes at a younger age also increase the risk of developing micro- and macro-vascular complications. A hallmark of type 2 diabetes mellitus is declining pancreatic β-cell function, which begins years before diagnosis and continues throughout the disease process. This deterioration continues despite initiation of numerous therapies, as these interventions lower glucose but do not directly slow β-cell decline and dysfunction. Defects in α-cell function are also important contributors to disease progression. Nonetheless, these subtle changes associated with disease progression of Type 2 diabetes are usually very difficult to monitor in a clinical setting.

Unlike patients with type 1 diabetes mellitus, type 2 patients are not absolutely dependent on insulin for life. However, many patients with type 2 diabetes are ultimately treated with insulin. Because these patients retain the ability to secrete some endogenous insulin, Type 2 patients are considered to require insulin but are not depend on insulin. Nonetheless, following initial diagnosis and unlike type 1 diabetes monitoring disease progression is a complex process. Thus, there is a clear need for early indicators of disease progression for Type 2 diabetes, as reversion to normal glucose regulation slows disease progression, and this is associated with a better prognosis and clinical outlook.

The number of people with type 2 diabetes has risen in recent years, and scientists estimate that just as many people could be suffering from the illness without realizing it. Research now indicates that the presence of specific gut bacteria may act as an indicator of disease progression.

A recent study examined the intestinal bacteria of 345 people, of which 171 had type 2 diabetes and managed to identify clear micro-biological indicators that could in the future be used to act as a useful indicator of disease progression and suggest that clinical intervention is required. (A metagenome-wide association study of gut microbiota in type 2 diabetes. Junjie Qin et al., 2012 doi:10.1038/nature11450.) In this case life style changes may be designed along with diet modification to prevent or delay the further onset of type 2 diabetes in subjects with impaired glucose tolerance.

Even though the scientific question remains as to whether the changes in gut bacteria influence the development of type 2 diabetes or whether the changes simply reflect that the person has presented with type 2 diabetes, any potential change in the microbial gut content may be used as a basis of i) an indicator of and ii) the progression of type 2 diabetes. In the paper the authors described a controlled meta-genome-wide association study based on next-generation shotgun sequencing of DNA extracted from the stool samples from a total of 345 Chinese people (171 had type 2 diabetes and the remainder were non-diabetic controls). None of the individuals had received any antibiotic treatment within 2 months before sample collection. The faecal samples were frozen immediately after collection.

After storage DNA was extracted using standard methods and a paired-end adaptor library with insert size of ~350 base pairs for every sample was generated and subjected to Next Generation Sequencing. Adaptor contamination and low-quality reads were discarded, and the remaining DNA sequences were electronically filtered to eliminate human DNA. From the remaining sequences derived from the non-diabetic controls an assessment of the type and number of bacteria present in a representative non-diabetic gut was generated and this was then compared to that generated from patients with type 2 diabetes. From these data a relationship was generated that correlated the presence of certain bacteria with the Type 2 diabetic gut.

The information generated from the non-diabetic controls actually provides a paradigm for future studies of the pathophysiological role of the gut bacterial meta-genome in other human disorders, and the potential usefulness for a gut-bacterial content approach for assessment of individuals at risk of such disorders.

Several scientific papers describe the use of a solid support paper sold under the trade name FTA® to collect, store and transport faecal samples for the molecular detection of certain microbial infections that are related to certain underlying disease states such as cancers (Fecal collection, ambient preservation, and DNA extraction for PCR amplification of bacterial and human markers from human faeces. Nechvatal J M, et al., J Microbiol Methods. 2008 February; 72(2):124-32). In addition the technology has been used to simply diagnose the presence of specific microorganism in the gut. Detection of *Cyclospora cayetanensis* in animal fecal isolates from Nepal using an FTA filter-base polymerase chain reaction method. Chu D M, et al., Am J Trop Med Hyg. 2004 October; 71(4):373-9. Evaluation of DNA extraction and PCR methods for detection of *Enterocytozoon bienuesi* in stool specimens. Subrungruang I, et al., J Clin Microbiol. 2004 August; 42(8):3490-4. Thus, faecal DNA irrespective of the origin may be preserved on the FTA paper.

BRIEF SUMMARY OF THE INVENTION

This invention relates to the use of solid supports such as FTA/FTA elute for the collection, storage and transportation of faecal samples to i) screen and ii) monitor certain disease or conditions such as the progression of diabetes mellitus type 2 [non-insulin-dependent diabetes mellitus (NIDDM) or adult-onset diabetes]. It is useful for providing both an early indication of disease onset and disease progression.

The inclusion of FTA cards with all its associated DNA preservation and anti-microbial properties into the claimed method or similar workflows significantly simplifies the process thereby facilitating an efficient and cost effective self-collection screening and disease progression monitoring system for type 2 diabetes. A similarly simplified method is also applicable to monitoring other disease states that are associated with an abnormal gut flora.

The related device and analysis system effectively stabilizes genetic material from gut flora organisms for monitoring NIDDM or other disease or conditions in a form suitable for archiving, transport and subsequent molecular analyses. Certain aspects of the invention further provide for the potential for automated processes.

Thus, in one embodiment, it is provided a method for detecting gut flora derived from human faeces, comprising acquiring a solid support containing human faeces; optionally amplifying nucleic acid from the human faeces; and detecting and quantifying the gut flora of interest.

In another embodiment, it is provided a method for assessing whether a person has type-2 diabetes, comprising
1) acquiring a solid support containing faeces from the person;
2) optionally amplifying nucleic acid for 16S rRNA of bacteria of interest from the human faeces;
3) detecting and quantifying the bacteria of interest by nucleic acid sequencing technique; and
4) assessing whether the person has type-2 diabetes, wherein the assessment is by
   a. calculating a ratio for the amount of butyrate-producing bacteria to the amount of sulphate reduction/oxidative stress resistance bacteria, an increase of the ratio from that of a healthy individual indicates the person has type-2 diabetes, or
   b. normalizing detected value of the 16S rRNA from the bacteria of interest to that of a control genomic DNA sequence from the human faeces, a change in normalized value from that of a healthy individual indicates the person has type-2 diabetes.

In still another embodiment, the invention provided a kit for detecting and quantifying gut flora from human faeces, comprising a solid support for collecting human faeces; and primer pairs for amplifying 16S rRNA sequence from bacteria of interest.

Further details and advantages of the present invention will appear from the description and claims below.

DETAILED DESCRIPTION OF THE INVENTION

Certain aspects of the invention describes the use of solid supports such as the Whatman FTA/FTA elute for the collection, storage and potential transportation of faecal samples to screen and monitor the progression of disease or condition, such as type 2 diabetes mellitus. The use of a solid support such as the FTA cards with all its associated nucleic acid preservation and anti-microbial properties in a workflows significantly simplifies the process.

The technology is highly suited for self-collection and preserves all nucleic acids irrespective of origin in a format that is useful for future molecular epidemiological studies of intestinal bacteria for use in a range of human diseases including type 2 diabetes. Thus a patient could carry out self-collection of faeces on to the solid support such as the FTA paper, then send the sample to centralized laboratories for screening. Thus it enables an efficient and cost effective self-collection screening and disease progression monitoring system for, e.g., type 2 diabetes. In addition this method is also applicable to other disease states that are associated with an abnormal distribution of gut flora.

Thus, certain embodiments of the invention provides a method for detecting gut flora derived from human faeces, comprising
1) acquiring a solid support containing human faeces;
2) optionally amplifying nucleic acid from the human faeces; and
3) detecting and quantifying the presence of gut flora of interest.

The term "Gut flora" refers to human cells and microorganisms found in the gut and the GI tract including prokaryotes, virus and eukaryotes.

The human faeces may be applied to the solid support and dried prior to the analysis. Certain solid supports contain chemical coating, which kills pathogen in the faeces and stabilizes the nucleic acid. These samples are stable over a long period of time, spanning days, months and even years, such as over 20 years. Typically, biological samples can be put on FTA paper and then dried for 3 hours and the DNA is stable for up to 23 years In certain embodiments, the solid support is fibrous, for example a cellulose fibre material, or a glass fibre/microfibre material.

In certain embodiments, the solid support is a porous polymer, for example porous membrane material such as polyester, polyether sulfone (PES), polyamide (Nylon), polypropylene, polytetrafluoroethylene (PTFE), polycarbonate, cellulose nitrate, cellulose acetate, alginate or aluminium oxide.

In certain other embodiments, the support surface is impregnated with chemicals, said chemicals including: a weak base; a chelating agent; an anionic surfactant; and/or a chaotropic agent such as guanidinium thiocyanate.

In certain other embodiments, the solid support is FTA paper, FTA Elute paper, or Whatman 903 paper.

Herein FTA (including FTA microcards, FTA indicating, and FTA classic) is a cellulose fibre paper treated with stabilizing chemicals, for example a weak base, a chelating agent and an anionic surfactant, whereby the support surface is impregnated with the stabilization chemicals. In this way the biological sample materials can be stored on the apparatus for many months or even years, thereby allowing time for transportation of the apparatus, if needed, to a laboratory, at an ambient temperature, and adequate recovery is then possible, simply by dissolving the stored sample and reagents.

FTA Elute herein describes similar paper but coated with a chaotropic agent such as guanidinium thiocyanate. Herein Whatman 903 describes uncoated cellulose fibre paper.

The solid supports described above are intended to be used in a generally flat configuration, but in the alternative, may for example be used on a roll.

The amplifying step may be performed using well known methods, such as polymerase chain reaction (PCR) or certain methods for isothermal amplification. In addition to PCR, other non-limiting examples of DNA amplification methods that may be used in the present invention include ligase chain reaction (LCR), self-sustained sequence replication (SSR), nucleic acid sequence-based amplification (NASBA) and amplification using Qβ-replicase. In some specific embodiments, the DNA template is amplified using rolling circle amplification (RCA). The RCA may either be a linear RCA (LRCA) or an exponential RCA (ERCA). In some embodiments, multiply-primed rolling circle amplification (MPRCA) may be employed for amplifying the DNA template. In some other embodiments, the DNA template may be amplified using a strand displacement amplification reaction (SDA). In yet another embodiment, the DNA template may be amplified using multiple displacement amplification (MDA).

Other amplification methods may include:

Helicase-dependent amplification is similar to traditional PCR, but uses a constant temperature rather than cycling through denaturation and annealing/extension steps. DNA Helicase, an enzyme that unwinds DNA, is used in place of thermal denaturation Nicking Enzyme Amplification Reaction referred to as NEAR, is isothermal, replicating DNA at a constant temperature using a polymerase and nicking enzyme.

Recombinase Polymerase Amplification (RPA). The method uses a recombinase to specifically pair primers with double-stranded DNA on the basis of homology, thus directing DNA synthesis from defined DNA sequences present in the sample. Presence of the target sequence initiates DNA amplification, and no thermal or chemical melting of DNA is required. The reaction progresses rapidly and results in specific DNA amplification from just a few target copies to detectable levels typically within 5-10 minutes.

In certain embodiments, the isothermal amplification is performed using phi29 DNA polymerase.

In certain embodiments, the amplifying step is performed using lyophilized reagents. Lyophilized reagents such as those illustra Ready-To-Go (RTG) products are well known.

In certain embodiments, the amplifying step is performed in the presence of cyclodextrin. Cyclodextrin acts as a sequestor of detergents which coat the outside of the solid support, thus improved DNA amplification assays maybe performed including direct amplification assays.

In certain embodiments, the amplifying step is performed by PCR using primer pairs for 16S rRNA amplification. Further descriptions of common primer pairs useful for 16S rRNA amplification is provided hereinbeflow.

In certain embodiments, the amplifying step is performed by multiplexed PCR. Multiplex-PCR uses multiple primer sets within a single PCR mixture to produce amplicons that are specific to different DNA sequences. This permits the simultaneous analysis of multiple targets in a single sample at once, thus additional information may be gained from a single test run that otherwise would require several times the reagents and more time to perform. For example, in testing for genetic mutations, six or more amplifications might be combined in a single reaction mixture. In the standard protocol for DNA Fingerprinting, 18-21 targets loci are amplified in a single PCR reaction.

In certain embodiments, the optional amplifying step or the detecting and quantifying step is carried out directly from punches excised from solid support containing human faeces. Thus, amplification and detection may be carried out directly from punches excised from solid support on which a biological sample (i.e., human faeces) has been applied. The punches containing the sample are added directly to amplification reactions in combination with cyclodextrin containing buffers that neutralize the chemistry associated with the FTA paper. This addition does not affect the efficiency of the amplification reaction. Simple "punch-ins" additions can be performed in which the excised punch (solid support plus sample) is washed to remove any potential inhibitory chemical or biological material prior to the addition to the amplification reaction.

In certain embodiments, the method for detecting gut flora derived from human faeces further comprising a step of purifying the nucleic acid from the solid support containing human faeces prior to the optional amplifying step.

Detecting and quantifying the presence of gut flora of interest may be achieved by detecting and quantifying the 16S rRNA of the bacteria of interest. In certain embodiments, detecting and quantifying the presence of gut flora of interest may be achieved by detecting and quantifying the 16S rRNA using next generation sequencing technique. In certain embodiments, detecting and quantifying the presence of gut flora of interest may be achieved by detecting and quantifying a signature nucleic acid sequence for each microorganism of interest using next generation sequencing technique.

In certain embodiments, the method for detecting gut flora derived from human faeces further comprises calculating a ratio for the amount of butyrate-producing bacteria to the amount of sulphate reduction/oxidative stress resistance bacteria, an increase of the ratio from that of a healthy individual indicates the person has type-2 diabetes.

In certain embodiments, the method for detecting gut flora derived from human faeces further comprises normalizing detected value of the 16S rRNA from the bacteria of interest to that of a control genomic DNA sequence from the human faeces, a change in normalized value from that of a healthy individual indicates the person has type-2 diabetes. In certain embodiments, the quantification of the nucleic acid from bacteria can be related by normalising the values to human genomic DNA in the same faeces sample. An exemplary gene which may be used is the reduced folate carrier SLC19A1 GenBank Number U19720.

In another aspect, the invention provides a method for assessing whether a person has type-2 diabetes, comprising
1) acquiring a solid support containing faeces from the person;
2) optionally amplifying nucleic acid for 16S rRNA of bacteria of interest from the human faeces;
3) detecting and quantifying the presence of the bacteria of interest by nucleic acid sequencing technique; and
4) assessing whether the person has type-2 diabetes, wherein the assessment is by
   a. calculating a ratio for the amount of butyrate-producing bacteria to the amount of sulphate reduction/oxidative stress resistance bacteria, an increase of the ratio from that of a healthy individual indicates the person has type-2 diabetes, or
   b. normalizing detected value of the 16S rRNA from the bacteria of interest to that of a control genomic DNA sequence from the human faeces, a change in normalized value from that of a healthy individual indicates the person has type-2 diabetes.

Certain details of the method for assessing whether a person has type-2 diabetes are similar to that described above for the method for detecting gut flora derived from human faeces. Furthermore, in certain embodiments, the nucleic acid sequencing technique is next generation sequencing.

In other embodiments, the amplifying step is carried out directly from punches excised from solid support containing human faeces.

In other embodiments, the method further comprising a step of purifying the nucleic acid from the solid support containing human faeces prior to the optional amplifying step.

In another aspect, the invention provides a kit for detecting and quantifying gut flora from human faeces, comprising a solid support for collecting human faeces; and primer pairs for amplifying 16S rRNA sequence from bacteria of interest. Certain elements of the kit have been described in detail above in the paragraphs describing the method for detecting gut flora derived from human faeces. Furthermore, in certain embodiments, the kit further comprises an amplification enzyme and a sequencing enzyme. Amplification enzymes and sequencing enzymes are well known in the art. In some embodiments, the amplification enzyme is in a lyophilized form. In still further embodiments, the lyophilized amplification enzyme also contains cyclodextrin.

Type 2 Diabetes Markers and Gut Flora

An analysis on the microbial content of the gut in patients with type 2 diabetes was performed by developing a shotgun DNA sequencing protocol. It was identified that a significant number of type 2-diabetes associated bacterial species and markers were able to demonstrate that patients with type 2 diabetes were characterized by a decrease in the abundance of some universal butyrate-producing bacteria and an increase in various opportunistic pathogens and the enrichment of other microbial functions such as sulphate reduction and oxidative stress resistance.

Faecal samples were collected from both type-2 diabetes patients and healthy volunteers. The samples were frozen immediately and subsequently underwent DNA extraction. DNA sequencing was performed using a paired-end library with an insert-size of 350 bp. End-adaptor contamination and low quality reads were discarded and human contamination sequences were filtered out.

Examples of micro-organism associated with the type-2-diabetes gut and from non-affected individuals is described below

TABLE I

| Type-2 Diabetes-enriched | Control-enriched |
| --- | --- |
| Akkermansia muciniphila | Clostridiales sp. SS3/4 |
| Bacteroides intestinalis | Eubacterium rectale |
| Bacteroides sp. 20_3 | Faecalibacterium prausnitzii |
| Clostridium bolteae | Haemophilus parainfluenzae |
| Clostridium hathewayi | Roseburia intestinalis |
| Clostridium ramosum | Roseburia inulinivorans |
| Clostridium sp. HGF2 | Faecalibacterium sp. |
| Clostridium symbiosum | |
| Desulfovibrio sp. 3_1_syn3 | |
| Eggerthella lenta | |
| Escherichia coli | |
| Alistipes sp. | |

One approach to identify the presence any of the organisms described above is to sequence the respective 16S rRNA gene. This gene is used for classification and identification of microbes, because it is present in most microbes and shows sufficient DNA sequence differences to facilitate differentiation. Therefore the gene is used for phylogenetic studies as it is highly conserved between different species of bacteria.

Common primer pairs for 16S rRNA gene amplification are described in the scientific literature.

TABLE II

| Primer name | Sequence (5'-3') |
| --- | --- |
| 8F | AGA GTT TGA TCC TGG CTC AG (SEQ ID NO: 1) |
| U1492R | GGT TAC CTT GTT ACG ACT T (SEQ ID NO: 2) |
| 928F | TAA AAC TYA AAK GAA TTG ACG GG (SEQ ID NO: 3) |
| 336R | ACT GCT GCS YCC CGT AGG AGT CT (SEQ ID NO: 4) |
| 1100F | YAA CGA GCG CAA CCC (SEQ ID NO: 5) |
| 1100R | GGG TTG CGC TCG TTG (SEQ ID NO: 6) |
| 337F | GAC TCC TAC GGG AGG CWG CAG (SEQ ID NO: 7) |
| 907R | CCG TCA ATT CCT TTR AGT TT (SEQ ID NO: 8) |
| 785F | GGA TTA GAT ACC CTG GTA (SEQ ID NO: 9) |
| 805R | GAC TAC CAG GGT ATC TAA TC (SEQ ID NO: 10) |
| 533F | GTG CCA GCM GCC GCG GTA A (SEQ ID NO: 11) |
| 518R | GTA TTA CCG CGG CTG CTG G (SEQ ID NO: 12) |
| 27F | AGA GTT TGA TCM TGG CTC AG (SEQ ID NO: 13) |
| 1492R | CGG TTA CCT TGT TAC GAC TT (SEQ ID NO: 14) |

Bacterial DNA sequences for the 16S rRNA gene are available on public databases such as NCBI, EzTaxon, Ribosomal Database Project etc.

1) EzTaxon-e. http://eztaxon-e.ezbiocloud.net/ The EzTaxon-e database is an extension of the original EzTaxon database. It contains comprehensive 16S rRNA gene sequences of taxa with valid names as well as sequences of uncultured taxa. EzTaxon-e contains complete hierarchical taxonomic structure (from phylum rank to species rank) for the domain of bacteria and archaea. (hun, J et al 2007; EzTaxon: a web-based tool for the identification of prokaryotes based on 16S ribosomal RNA gene sequences. Int J Syst Evol Microbiol 57, 2259-2261.

2) Ribosomal Database Project. http://rdp.cme.msu.edu/ The Ribosomal Database Project (RDP) is a curated database that offers ribosome data along with related programs and services. The offerings include phylogenetically ordered alignments of ribosomal RNA (rRNA) sequences, derived phylogenetic trees, rRNA secondary structure diagrams and various software packages for handling, analyzing and displaying alignments and trees. The data are available via ftp and electronic mail. Certain analytic services are also provided by the electronic mail server, Larsen N, et al 1993, The ribosomal database project. Nucleic Acids Res. July 1; 21(13):3021-3.

3) SILVA. SILVA provides comprehensive, quality checked and regularly updated datasets of aligned small (16S/18S, SSU) and large subunit (23S/28S, LSU) ribosomal RNA (rRNA) sequences for all three domains of life (Bacteria, Archaea and Eukarya), Elmar Pruesse, et al 2007, Nucleic Acids Res. SILVA: a comprehensive online resource for quality checked and aligned ribosomal RNA sequence data compatible with ARB. December; 35(21): 7188-7196.

4) Greengenes. The greengenes web application provides access to the 2011 version of the greengenes 16S rRNA gene sequence alignment for browsing, blasting, probing, and downloading. The data and tools presented by greengenes can assist the researcher in choosing phylogenetically specific probes, interpreting microarray results, and aligning/annotating novel sequences.

FTA and Stool Samples; Bacterial and Human Targets

A study was performed in which fresh human faeces was applied to Whatman FTA cards. The resultant purified DNA was characterised using PCR amplification of bacterial and human DNA markers. Little or no PCR inhibition was detected indicating that the stool samples contained no compounds that were considered inhibitory to the PCR reaction.

Fifteen fresh stool samples (0.2 g) were applied to Whatman FTA cards. According to manufacturer's instructions the faeces was allowed to dry for 2 h at room temperature, and the cards placed in a protective barrier pouch with silica gel desiccant packet and stored for 5 days at ambient temperature prior to subsequent DNA extraction and analysis.

DNA was extracted from the material (0.2 g) applied to the FTA cards as twenty 2.0 mm diameter punches (i.e. each punch contained approximately 0.01 g of faeces) and using the following commercially-available kits; Qiagen RNA/DNA Mini (catalogue number 14123), Qiagen QIAamp DNA Stool Min (catalogue number 51504) and Mo-Bio Fecal kit (Mo-Bio, Carlsbad, Calif.). All procedures followed manufacturers' recommendation except for the following modifications. For the Qiagen RNA/DNA Mini kit; card samples were not subjected to a lysozyme pre-treatment but were incubated on ice for 10 min with 200 μl TE added. Following the incubations, 0.2 g of sterile DNase-free sand and 1 ml of GITC buffer (4 M guanidium thiocyanate, 10 mM Tris HCl [pH 7.0], and 1 mM EDTA [pH 7.0], 0.5% 2-mercaptoethanol) were added and samples vortexed for 20 min. Samples were then centrifuged at 10,000×g for 20 min and supernatant transferred to new tubes. Following centrifugation, 0.5 ml of QRL-1 buffer was added and the new solutions passed through an 18 G needle 10 times. Next, a further 0.5 ml QRV-1 buffer was added and the samples were mixed well, and centrifuged (10,000×g) at 4° C. for 20 min. The supernatant was transferred to a new tube and the nucleic acid precipitated using 0.8 volumes of ice-cold isopropanol. All subsequent extraction was according to the manufacturer's instructions. All resultant purified DNA was stored at −80° C.

Since the presence of PCR inhibitors in stool extracts could affect the accuracy of the bacterial real-time PCR measurements, the amount of inhibition, was estimated by two independent methods. The first method compared the change in the average Ct for a 10-fold DNA dilution. In the absence of PCR inhibition, the expected result is that higher amounts of starting DNA will result in a lower value of Ct. Assuming 100% PCR efficiency (i.e., a doubling of the amplicon concentration each cycle) a comparison of average shifts in Ct values with this theoretical performance (in the absence of inhibition) allows an estimate on the concentration of PCR inhibitors. The second compared the RFU values produced by the final PCR product of the undiluted DNA sample to the final RFU for diluted and therefore potentially less inhibited samples. The RFU of the final PCR product is a measure of the total amount of DNA produced, possibly modified by inhibition. A lower final RFU for the undiluted DNA sample, compared to that obtained at 1:10 or 1:100 would indicate the presence of inhibition.

Results derived from method 1 indicated that no measurable PCR inhibition was presence providing that the DNA sample was diluted to 1:100, whilst method 2 identified relatively little inhibition.

DNA quantitation was performed using a fluorometric Quant-iT™ Picogreen assay (Molecular Probes). The amount of faecal DNA in each sample was compared to the relative fluorescence units of Phage λ DNA standards. Results irrespective of the extraction kit used indicated that approximately 2 ug of DNA could be extracted reproducibly from the 0.01 g of faecal on each 2.0 mm FTA punch.

Real-time PCR assays were also performed. The presence of DNA derived from several bacterial species was evaluated in order to identify the presence of a high abundance and consistent bio-marker source. As a result *Bacteroides* DNA in the stool samples was used to represent the presence of bacterial DNA.

Real-time SYBR-Green (Molecular Probes) PCR was performed using a 16S rDNA Bacteroides target. The PCR reagent mixture consisted of 12.5 μl SYBR-Green II master mix (containing Taq polymerase, dNTP's, $MgCl_2$, SYBR-Green fluorescent dye, fluorescein (for signal normalization), and Tris buffer), 11.0 μl water, 0.25 μl each of 20 pmol/μl Bac32F (SEQ ID NO:15, 5'-AACG CTAG CTA-CAGGC TT-3') and 708R (SEQ ID NO:16, 5'-CAAT CGGA GTTC TTCG TG-3') primers, which yields a 676 bp amplicon and 1.0 μl of the template DNA. The PCR was performed in duplicate on undiluted DNA (1:1) and on dilutions of 1:10, 1:100, and 1:1000. *Bacteroides fragilis* (ATCC 25285) DNA, served as a positive control. The PCR protocol involved an initial denaturation step of 94° C. for 2 min, followed by 35 cycles of 94° C. denaturation for 20 s, 62° C. primer annealing for 20 s (decreasing in decrements of 0.3° C. per cycle), and 72° C. extension for 45 s; and a final 72° C. for 10 min. PCR products were verified via agarose gel(s) and/or melt-curve analysis.

The amount of *Bacteroides* Spp. DNA in experimental faecal samples was determined from the Ct values measured for the 1:100 samples (a dilution at which the above experiments indicated that PCR inhibition did not occur; see later). The relationship between the amounts of *Bacteroides* Spp. DNA and total DNA measured by Picogreen indicates that the average percentage of total DNA in the sample that is *Bacteroides* Spp. DNA was approximately 38%.

Stool DNA samples were also analysed for human genomic DNA, (reduced folate carrier SLC19A1; Genbank U19720), using a nested PCR approach. In the primary PCR, the PCR reaction mix contained 5 µl GeneAmp® 10×PCR Buffer II (Applied Biosystems, N8080130), 4 µl dNTPs (Applied Biosystems, N8080007), 3 µl 25 mM $MgCl_2$ (Applied Biosystems N8080130), 2.5 µl dimethylsulfoxide, 1.0 µl of each primer (10 pmol/µl each of hRFC2308R (SEQ ID NO:23, 5'-AAGA GCAC CAAG GATG ACCA GCAA TGTC-3') and hRFC1525F (SEQ ID NO:24, 5'-AGGA GAAG GCAG CACA GGCA CTAG)-3', 0.5 µl 5 U/µl Taq DNA polymerase (Promega, PR-M8291), 0.2-4 µl template DNA solution, and water to a final volume to 50 µl. The second round PCR mixture was the same, but utilized 2.0 µl of first round PCR product for the template and the nested primers hRFC1857R (SEQ ID NO:25, 5'-GCGC CCGA GAAT CACT TGGT TTCA CATT-3') and hRFC1643F (SEQ ID NO:26, 5'-GGAG CAGA GACA GAGC GACC CATA CCTG-3'). The primary PCR thermocycle consisted of 94° C. for 3 min initial denaturation, 35 cycles of amplification (30 s, 94° C.; 45 s, 64° C. primer annealing, 1 min 72° C. elongation), and 7 min final 72° C. elongation. Second round PCR was identical except only 32 cycles were used and the annealing step was at 62° C. PCR products were separated on 2% agarose gels stained with ethidium bromide.

Results indicated that several of the FTA extracts did not produce a PCR product corresponding to the reduced folate carrier SLC19A1 gene when tested at the 1:100 dilutions. However, when diluted further the appropriate product was obtained, indicating that a degree of PCR inhibition may have been present at the higher concentrations.

This study clearly demonstrates that bacterial and human DNA can be stored at room temperature as faecal samples on Whatman FTA cards, for duration of at least 5 days. DNA extraction is feasible using commercially-available kits. The quality and purity of the extracted DNA is sufficient to support PCR-based amplification applications.

DNA Sequencing After Sample Application to Whatman FTA Cards.

A study was performed which describes a method used to differentiate between *Candida albicans* and *Candida dubliniensis* based upon PCR-sequencing. The method was also used to compare a traditional but less reliable phenotypic differentiation. Nested PCR amplification of D1/D2 region of the ribosomal large subunit rLSU gene was performed after the fungal DNA was extracted from Whatman FTA filter paper.

A yeast suspension was prepared from cultures grown for 48 h on SDA medium and 200 µl was applied directly to Whatman indicating FTA microcards. Cards plus sample were placed, open, in a microwave set at 800 W while still damp and were subjected to two cycles of 30 s on full power, with a pause of at least 30 s between each cycle. Resultant dried cards were then stored at room temperature in sealed plastic bags containing desiccant. Punches (2 mm in diameter) were removed from dried FTA filters using a Harris micro-punch and then washed as follows; two washes for 1 min each with 100 µl of Whatman FTA wash reagent, followed by two washes for 1 min each with 100 µl TE buffer (10 mM Tris-HCl [pH 7.5], 0.1 mM EDTA). Washed filters were then dried for 5 min at 55° C., and PCR reaction mixtures were added directly.

Nested PCR amplification of D1/D2 region of the rLSU gene was performed with the primers ITS1 (SEQ ID NO:17, 5'-TCC GTA GGT GAA CCT GCG G-3') and D2R (SEQ ID NO:18, 5'-TTG GTC CGT GTT TCA AGA CG-3') in the first reaction and D1F (SEQ ID NO:19, 5'-GCA TAT CAA TAA GCG GAG GA-3') and D1D2R1 (SEQ ID NO:20, 5'-TCC CTT TCA ACA ATT TCA CG-3') in the second reaction. For the first PCR, reactions (50 µl) were performed in the presence of 200 µM concentrations of each deoxynucleoside triphosphate, 250 nM concentrations of the appropriate primers, 10×PCR buffer and 1.25 U Taq DNA polymerase (Qiagen), and a single filter punch.

The PCR conditions for first reaction were as follows: an initial denaturation at 94° C. for 5 min followed by 35 cycles of denaturation at 94° C. for 30 s, annealing at 51° C. for 45 s, and extension at 72° C. for 90 s, with a final extension at 72° C. for 5 min on a GeneAmp PCR Systems 9700 thermocycler (Applied Biosystems). The second PCR reactions (50 µl) were performed in the presence of 200 µM concentrations of each deoxynucleoside triphosphate, 250 nM concentrations of the appropriate primers, 10×PCR buffer and 1.25 U Taq DNA polymerase and 4 µl of the first PCR product. The PCR conditions for second reaction were as follows: an initial denaturation at 94° C. for 5 min followed by 35 cycles of denaturation at 94° C. for 30 s, annealing at 52° C. for 45 s and extension at 72° C. for 90 s, with a final extension at 72° C. for 5 min on a GeneAmp PCR Systems 9700 thermocycler. PCR products were purified using ethanol purification, and cycle sequencing reactions in forward and reverse directions using the appropriate primer sets were performed using a Big Dye terminator ready reaction kit (Applied Biosystems). The sequencing products were purified by DyeEx kit (DyeEx 2.0 Spin Kit; Qiagen) and were then analyzed on an ABI 3130 Genetic Analyzer (Applied Biosystems) and analyzed with Sequencing Analysis (ver5.1) software (Applied Biosystems). The resultant DNA sequences of organisms were identified using NCBI BLAST searches against fungal DNA sequence databases.

The results of automatic sequencing of the PCR amplicons (including PCR primer sites) ranged from 307 to 350 bp and the sequences of all 20 isolates exhibited 100% similarity to the known *C. dubliniensis* D1/D2 region of the rLSU gene. The conclusion was that DNA sequence analysis is significantly more reliable than the traditional phenotypic identification method. This study demonstrated that DNA extracted from FTA cards is of sufficient quality to support PCR-based DNA sequencing.

RTG Combination

The illustra Ready-To-Go PCR Beads technology consists of pre-formulated and pre-dispensed, freeze-dried reagents mix in a bead format for amplifications reactions such as PCR, RT-PCR (reverse transcriptase PCR) and WGA (whole genome amplification). The reagents contain all the components necessary for nucleic amplifications including the appropriate enzymes, dNTPs etc. The enabling property of these reagents is that they can be stored for a pro-longed time periods at ambient-temperature with no deterioration in amplification efficiency. To initiate the reaction only the addition of the appropriate template and primers are required.

Several illustra Ready-To-Go formats exist including GenomiPhi V3 DNA Amplification Kit, Ready-To-Go RT-PCR Beads and PuReTaq Ready-To-Go PCR. To illustrate the combination of FTA sample collection cards and the ready-to-go technology the following experimental study was performed in which blood was applied to FTA cards, DNA eluted, and subjected to whole genome amplification. To demonstrate the quality and purity of the WGA-amplified restriction enzyme digestion and DNA STR profiling was performed.

Whatman FTA cards are chemically-coated cellulose-based sample collection tools that simplify the collection, shipment, storage, and purification of nucleic acids from a wide variety of sources. Biological samples are applied directly onto the card. Chemicals in the FTA card lyse the cells, denature proteins, and immobilize the nucleic acids. After drying, DNA is protected from enzymatic, microbial, oxidative, and free-radical damage. The samples can be stored for years at room temperature. For analysis or use of DNA stored on FTA cards, a small disc is cut from the sample area. For typical blood samples (assuming 5000 white blood cells per µl of whole blood), a 1.2 mm disc from a dried blood spot may contain approximately 5 ng of DNA, and a 3 mm disc approximately 30 ng. Therefore, the amount of genomic DNA that is obtained from the cards can be limiting, and additional larger samples are often required for complete genomic analyses.

A simple method to overcome this limitation is the use of whole genome amplification. This study describes the purification of DNA from FTA dried blood spot samples in a form that is suitable for whole genome amplification (WGA) using the commercially-available illustra Ready-To-Go GenomiPhi V3 DNA Amplification Kit. This method was shown to consistently yield over 15 micrograms of high molecular weight DNA from single 1.2 mm or 3 mm punched discs. The DNA is of sufficient quality to support downstream applications such as PCR-based short tandem repeat (STR) profiling.

The illustra Ready-To-Go GenomiPhi V3 DNA Amplification Kit from GE Healthcare Life Sciences provides an ambient temperature-stable reaction mix for WGA. Using Phi29 DNA polymerase and random hexamer primers, isothermal WGA is achieved by a multiple strand displacement amplification mechanism, producing microgram quantities of high molecular weight copies from nanogram amounts of genomic DNA. The proofreading 3'-5' exonuclease activity of Phi29 DNA polymerase ensures high fidelity amplification. This system provides excellent genome coverage and is an established method used successfully in many genomics applications.

To prepare dried blood spots, 60 µl of human blood was spotted onto an FTA Classic Card (GE Healthcare; WB120205), allowed to dry overnight at room temperature and stored desiccated until required. Both 1.2 and 3 mm discs were punched from the FTA dried blood spot using sterile Harris Micro punches with a cutting mat (see detailed procedure described below). Triplicate punches for each diameter were processed and subjected to WGA as described below. Control WGA reactions were carried out using genomic DNA purified from the same blood sample using the illustra blood genomicPrep Mini Spin Kit (GE Healthcare; 28-9042-64). Amplification products were quantified using Quant-iT™ PicoGreen™ dsDNA Reagent (Life Technologies; P7589).

From the dried blood spot region of the FTA card, 1.2 or 3 mm diameter discs were excised and placed in a microcentrifuge tube. FTA Purification Reagent (GE Healthcare; WB120204; 200 µl for 1.2 mm and 500 µl for 3 mm discs) was added and the discs were agitated by simple pipetting up and down. The discs were incubated for 5 min at room temperature after which the liquid was carefully removed using a pipette. This washing procedure was repeated twice for a total of 3 washes. TE buffer (pH 8.0; 200 µl for 1.2 mm and 500 µl for 3 mm discs) was added to each tube and mixing was accomplished by pipetting up and down. The discs were incubated for 5 min at room temperature. After which the liquid was carefully removed using a pipette. This procedure was repeated twice after which as much liquid as possible was removed. Cell lysis/denaturation solution (10 µl; 400 mM KOH, 5 mM EDTA) was added to each damp disc and agitated by gentle tapping. The discs and subsequent cell lysate were incubated on ice for 10 min followed by the addition of 20 µl of neutralization buffer (300 mM Tris-HCl, 200 mM HCl). After mixing and storage on ice, 2 µl of each neutralized lysate was added to 8 µl of PCR-grade water.

WGA was achieved by adding 10 µl of the 2× denaturing buffer from the Ready-To-Go GenomiPhi V3 DNA Amplification Kit (25-6601-24, -96, or -97), and pipetting the whole resultant 20 µl onto a Ready-To-Go GenomiPhi V3 bead. The mixture was agitated by gently pipetting up and down. The sample was incubated at 30° C. for 2 h followed by 65° C. for 10 min and then 4° C. The WGA-products was stored at −20° C.

To confirm amplification efficiency and to determine whether the amplified DNA was restriction endonuclease sensitive, WGA reaction were digested with EcoRI restriction endonuclease and run on a 1% agarose gel alongside the corresponding undigested WGA reaction. For each digestion reaction, 10 µl of amplified product was incubated with 10 units of enzyme overnight at 37° C. A positive WGA control, which was amplified from DNA purified using the illustra blood genomicPrep Mini Spin Kit, was included together with a 'no template' WGA control.

To assess the quality of WGA-amplified DNA, STR genotyping analysis was performed. WGA-amplified DNA or unamplified control DNA (2 ng) was subjected to STR analysis using the AmpF1STR™ Identifiler™ PCR Amplification Kit (Applied BioSystems; 4322288) according to the manufacturer's protocol. STR reactions were performed on a GeneAmp™ PCR System 9700. Capillary electrophoresis was conducted on a 3130xL Genetic Analyzer followed by analysis using GeneMapper™ ID v3.2 Software.

Results from the Picogreen ds Reagent kit indicated that the Ready-To-Go GenomiPhi V3 kit consistently amplified between 15 and 18 µg from DNA applied to FTA cards derived from both 1.2 and 3 mm punched discs. Agarose gel analysis indicated that undigested WGA product from FTA dried blood spots was of high molecular weight (>10 kb). In samples digested with the enzyme EcoRI, DNA transitions from a high molecular weight to a lower molecular weight smear was clearly visible. No amplified DNA was visible for the 'no template' WGA control (data not shown).

DNA was eluted from FTA dried blood spots according to the alkaline denaturation protocol, amplified with Ready-To-Go GenomiPhi V3, and subjected to STR amplification. STR analysis produced the expected allele calls for the full profile of 15 alleles (plus amelogenin) for all replicates tested and was concordant with the unamplified control DNA (data not shown)

This study demonstrated that the illustra Ready-To-Go GenomiPhi V3 DNA Amplification Kit can be effectively combined with sample collection on FTA cards to generate microgram quantities of high molecular weight DNA from 1.2 and 3 mm punched discs. A simple alkaline elution protocol that facilitates elution of DNA from FTA dried blood spots in a form that is suitable for whole genome amplification. Subsequent STR analysis of DNA amplified from FTA discs provided full profiles with all alleles correctly identified.

The combination of dried samples on FTA with the illustra Ready-To-Go GenomiPhi V3 DNA Amplification Kit helps to preserve valuable samples and enables researchers to generate sufficient high-quality DNA from those samples for multiple downstream applications. In addition, the combination of FTA cards and Ready-to-go formats provide an ambient temperature stable solution from sample collection to whole genome amplification, facilitating logistics and study design particularly in remote areas or settings with limited infrastructure.

Inclusion of Cyclodextrin in RTG Mix for Direct PCR
Chemicals and Materials Used A list of the chemicals and their sources is given below:
FTA papers for storing nucleic acid were obtained from GE Healthcare UK Limited;
Genomic DNA (Promega product code G152A);
1 kb DNA ladder (Promega product code G571A);
Harris Uni-core punch, 1.2 mm (Sigma, Catalogue number Z708860-25ea, lot 3110);
OmniKlentaq Polymerase (Mo Bio Inc, catalogue code 1225-250);
Deoxyribonucleotide triphosphate (dNTP) (Life Tech);
PCR Grade Bovine Serum Albumin (Life Tech);
Forward and reverse β-globin primer (Sigma Genosys)

```
β-globin 1.3 forward
                                   (Seq ID No. 21)
5'-TTAGGCCTTAGCGGGCTTAGAC-3'
and β-globin 1.3 reverse
                                   (Seq ID No. 22))
5'-CCAGGATTTTTGATGGGACACG-3';
```

α-cyclodextrin (Fluka code 28705) and Sterile water (Sigma Product code W4502).
Excipient mix:
Ficoll 70 (GE Healthcare);
Ficoll 400 (GE Healthcare) and
Melezitose (Sigma)
Cycle Sequence Mix 10×:
Trizma (Sigma);
KCl (Sigma);
MgCl (Sigma) and
Nuclease-free water (Sigma)
Exchange buffer:
Tris/HCl pH8.5 (Sigma);
1M $CaCl_2$ (Sigma);
1.0M $MgCl_2$ (Sigma);
2.0M KCl (Sigma) and
RHODAFAC RE-960 (7% RE960) (Kao Chemicals)
Experimental Results
DNA Measurement from Cellulose Matrices Using qPCR.
PCR reagents were combined with cyclodextrin and lyophilized.
Samples were combined with the lyophilized nucleic acid amplification composition in a 96 well plate.
PCR reaction was set up as follows:
Blood-spotted FTA was added to a well with a nucleic acid amplification reagent cake that contained cyclodextrin or did not contain cyclodextrin. Standards and samples were added to the appropriate wells. The plates were centrifuged at 1000 rpm for 1 minute and sealed. PCR was carried out on an MJ Research PTC-200 Thermo Cycler following the manufacturer's user instructions.

The thermal cycling conditions were: 95° C. for 5 min, 95° C. for 30 sec, 55/65° C. for 1 min, 72° C. for 2 min followed by 35 cycles of: 95° C. for 30 sec, 55/65° C. for 1 min, 72° C. 2 min, followed by 72° C. for 10 mins.

Following amplification, visualization of PCR products was achieved using agarose gel electrophoresis (1×TAE buffer, 1% agarose gel). The data from PCR amplification of unwashed blood-spotted FTA paper with nucleic acid amplification reagent cakes with or without α-cyclodextrin shows the presence of an unambiguous band in the presence of cyclodextrin; the band is absent without the addition of cyclodextrin (data not shown).

FTA Elute & Multiple Downstream Applications

A sample disc was excised manually from the centre of an indicating FTA elute (iFTAe) card using a Harris 3 mm micro-punch (WB100038) or a Harris 3 mm Uni-Core (WB100039) and a cutting mat. Depending upon the amount of DNA required one to four, 3 mm punches can be used. The excised discs were placed into a sterile 1.5 ml microcentrifuge tube. The iFTAe sample collection paper is coloured purple but on the application of an aqueous-based buccal cell sample changes colour. This colour change can be used to indicate the location of the sample.

To prevent cross contamination between samples, the head of the punching device is cleaned after each excision by performing three sequential cleaning punches using a separate iFTAe card that does not contain any applied biological sample.

As a control iFTAe cards that do not contain biological samples were also subjected to this DNA extraction protocol and on completion the resultant solution was used in all downstream diagnostic tests. These represented paper-only negative controls.

All punches were washed by adding 1 ml of room temperature sterile water to the tube and vortex for 3×5 seconds (i.e., 15 seconds in total). An efficient vortex is essential to maximise DNA yield. Using a sterile pipette tip, the wash solution was immediately removed from the tube. For optimal DNA extraction only 1 sample is processed at a time in order to reduce the amount of time that the disc is in contact with the wash solution. Using a sterile forceps or a pipette tip, the disc was transferred to either a sterile 1.5 ml mirco-centrifuge tube for low throughput DNA extraction or a well of a sterile 96 well PCR plate for a medium throughput.

Using the low throughput DNA extraction method, once all samples had been transferred to tubes, 60 µl of sterile water was added. The discs were completely immersed in the sterile water by centrifuging the tubes for 10 seconds at 10,000 rpm in a micro-centrifuge. The tubes were transferred to a heating block and heated at 98° C. for 30 minutes. At the end of the incubation period, the samples were removed and pulse vortexed either 60 times (1 pulse/second), or vortex continuously for 60 seconds.

Finally, the tubes were centrifuged at 10,000 rpm for 30 seconds in a micro-centrifuge. The DNA-containing eluate was transferred to a separate sterile 0.5 ml microfuge tube. These were either used immediately or stored at +4° C. if samples are to be used within a week or at −20° C. if storage is required for longer than 1 week.

Following the medium throughput DNA extraction, once all samples were transferred to the PCR plate, 60 µl of sterile water was added to each well and a plate seal applied to the top surface. To ensure that the discs were completely immersed in the water the plate was centrifuged for 2 minutes at ~12,000 rpm. On occasions when an increased DNA concentration was required the volume of water added was reduced to 30 µl.

The PCR plate was transferred to a heating block set at 98° C. for 30 minutes. At the end of the incubation period, the PCR plate was removed (ensuring that the seal is in still place) and the plate was shaken on a plate shaker set at maximum speed for 60 seconds. Once again an effective vortex was required for optimal DNA elution. The plate was centrifuge at ~12,000 rpm for 2 minutes and the resultant eluate containing the extracted DNA was transferred to a separate well of a sterile PCR plate. These were either used immediately or stored at +4° C. if samples are to be used within a week or at −20° C. if storage is required for longer than 1 week.

The DNA purified from the FTA Elute punches was subjected to various experimental techniques to demonstrate the quality of the purified DNA.

Quantitative PCR; samples were collected from 10 separate individuals onto FTA Elute cards and the cards were allowed to dry completely. Punches (3.0 mm) were extracted according to the water and heat elution protocol in a final volume of 100 µl. Approximately 2.5 µl of the purified DNA was added to the real time PCR mixture and amplified using the Yo-Pro 1 DNA binding dye (Invitrogen). All DNA samples successfully generated the appropriate real time PCR products with an average Ct of 26.58 which equals 22.14 ng of DNA in the 100 µl final volume (data not shown).

Biological samples dried on FTA Elute for 0, 2 and 8 years served as the DNA templates for WGA and analysis for SNP 1004. Purified DNA was subjected to whole genome amplification (WGA) using the REPLI-g Mini kit (Qiagen). The amplified DNA then underwent genotyping using TaqMan reagents targeted at the SNP 1004 locus. Results (not shown) demonstrate excellent allelic discrimination and were comparable to results obtained using commercially-available genomic DNA. These results demonstrated that DNA stored and purified from FTA Elute can serve as an effective template for DNA amplification using WGA and that the quality was sufficient to support future genotyping studies.

In order to test the quality of the DNA purified from FTA Elute, genotyping by DNA sequencing was performed using the DNA from 10 individuals. A 1.05 kb fragment from exon 1 of the 2B15 variant of the UDP-glucuronosyltransferase (UGT) gene was amplified from DNA derived from samples applied to FTA. The PCR product was treated with ExoSAP-IT™ (USB). These samples were then subjected to DNA sequencing using the ABI Big Dye™ v 1.1 and were carried out on an MJ Research Tetrad™ instrument. Sequencing reactions were cleaned up using ABgene Dye Terminator Removal Kits and run on an ABI Prism™ 3100 instrument. The sequence generated was scrutinised for the G>T polymorphism at the D85Y loci. Representations of homozygous wild type G/G (5 individuals), heterozygous wild type/ mutant G/T (2 individuals) and homozygous mutant T/T base (3 individuals) pair changes were detected.

Many labs perform multiplex gene deletion assays using end-point PCR and agarose gel electrophoresis as a means of genotyping. The presence or absence of bands for a large deletion is clearly visible on such gels. A multiplex PCR was performed with DNA purified from FTA Elute to detect a deletion in the UGT2B17 gene. The wild type and mutant genes are demonstrated by bands of 316 bp and 884 bp, respectively. Buccal call samples were obtained from 10 individuals known to be either heterozygous or homozygous for the mutation. These were applied to FTA elute and stored. When required the DNA was extracted and subjected to the UGT2B17 genotyping. Of the 10 individuals, 9 exhibited the PCR amplicons associated with the heterozygous genotype and the other the homozygous mutation (data not shown).

The ability to perform multiplex PCR amplifications using multiple primers is dependent upon high quality DNA. The absence of any mis-priming and non-specific banding patterns confirms that the DNA purified from samples applied to FTA Elute is of good quality and less than 1 ng is required to yield clean unambiguous bands in the multiplex PCR.

REFERENCES

Junjie Qin et al 2014 Nature. 2012 Oct. 4; 490(7418):55-60
Nechvatal et al 2008 (Journal of Microbiological Methods 72 (2008) 124-132)
Kiraz N et al 2014 Mycopathologia, 177:81-86
Whole Genome Amplification from dried blood spots using the illustra Ready-to-Go genomiPhi V3. Application Note 29-0622-44 AA
Whatman FTA Elute Data File 28-9844-02 AA While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

We claim:

1. A method for detecting gut flora derived from human faeces, comprising
   1) acquiring a solid support containing human faeces, wherein the solid support comprises cellulose fibre material, wherein the support has a surface impregnated with chemicals including a weak base, a chelating agent, an anionic surfactant and/or a chaotropic agent;
   2) amplifying nucleic acid from the human faeces, wherein the amplifying step is performed by multiplexed PCR using primer pairs for 16S rRNA from the flora using lyophilized phi29 DNA polymerase in the presence of cyclodextrin; and
   3) detecting and quantifying from the amplified nucleic acid a ratio of an amount of butyrate-producing bacteria to an amount of sulphate reduction/oxidative stress resistance bacteria.

2. The method of claim 1, wherein the human faeces had been applied to the solid support and dried prior to step 1.

3. The method of claim 1, wherein the solid support further comprises a porous polymer, for example porous membrane material such as polyester, polyether sulfone (PES), polyamide (Nylon), polypropylene, polytetrafluoroethylene (PTFE), polycarbonate, cellulose nitrate, cellulose acetate, alginate or aluminium oxide.

4. The method of claim 1, wherein the chaotropic agent is guanidinium thiocyanate.

5. The method of claim 1, wherein the amplifying step or the detecting and quantifying step is carried out directly from punches excised from solid support containing the human faeces.

6. The method of claim 1, further comprising a step of purifying the nucleic acid from the solid support containing the human faeces prior to the amplifying step.

7. The method of claim 1, wherein detecting and quantifying the 16S rRNA is by next generation sequencing technique.

8. The method of claim 1, wherein detecting and quantifying the gut flora of interest is by detecting and quantifying a signature nucleic acid sequence for each microorganism of interest using next generation sequencing technique.

* * * * *

SEQUENCE LISTING

```
<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
agagtttgat cctggctcag                                              20

<210> SEQ ID NO 2
```

```
<211> LENGTH: 19
<212> TYPE: DNA
<213> ORGANISM: Artificial Sequence
<220> FEATURE:
<223> OTHER INFORMATION: Synthetic primer

<400> SEQUENCE: 2
ggttaccttg ttacgactt                                                    19

<210> SEQ ID NO 3
<211> LENGTH: 23
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (8)..(8)
<223> OTHER INFORMATION: Y is C or T.
<220> FEATURE:
<221> NAME/KEY: misc_feature
<222> LOCATION: (12)..(12)
<223> OTHER INFORMATION: K is G or T.

<400> SEQUENCE: 3
taaaactyaa akgaattgac ggg                                               23

<210> SEQ ID NO 4
<211> LENGTH: 23
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (9)..(9)
<223> OTHER INFORMATION: S is G or C.
<220> FEATURE:
<221> NAME/KEY: misc_feature
<222> LOCATION: (10)..(10)
<223> OTHER INFORMATION: Y is C or T.

<400> SEQUENCE: 4
actgctgcsy cccgtaggag tct                                               23

<210> SEQ ID NO 5
<211> LENGTH: 15
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: Y is C or T.

<400> SEQUENCE: 5
yaacgagcgc aaccc                                                        15

<210> SEQ ID NO 6
<211> LENGTH: 15
<212> TYPE: DNA
<213> ORGANISM: Artificial Sequence
<220> FEATURE:
<223> OTHER INFORMATION: Synthetic primer

<400> SEQUENCE: 6
gggttgcgct cgttg                                                        15
```

```
<210> SEQ ID NO 7
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (17)..(17)
<223> OTHER INFORMATION: W is A or T.

<400> SEQUENCE: 7
gactcctacg ggaggcwgca g                                        21

<210> SEQ ID NO 8
<211> LENGTH: 20
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (15)..(15)
<223> OTHER INFORMATION: R is A or G.

<400> SEQUENCE: 8
ccgtcaattc ctttragttt                                          20

<210> SEQ ID NO 9
<211> LENGTH: 18
<212> TYPE: DNA
<213> ORGANISM: Artificial Sequence
<220> FEATURE:
<223> OTHER INFORMATION: Synthetic primer

<400> SEQUENCE: 9
ggattagata ccctggta                                            18

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
gactaccagg gtatctaatc                                          20

<210> SEQ ID NO 11
<211> LENGTH: 19
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (9)..(9)
<223> OTHER INFORMATION: M is A or C.

<400> SEQUENCE: 11
gtgccagcmg ccgcggtaa                                           19

<210> SEQ ID NO 12
<211> LENGTH: 19
<212> TYPE: DNA
<213> ORGANISM: Artificial Sequence
<220> FEATURE:
<223> OTHER INFORMATION: Synthetic primer
```

<400> SEQUENCE: 12
gtattaccgc ggctgctgg                                                    19

<210> SEQ ID NO 13
<211> LENGTH: 20
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (12)..(12)
<223> OTHER INFORMATION: M is A or C.

<400> SEQUENCE: 13
agagtttgat cmtggctcag                                                   20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
cggttacctt gttacgactt                                                   20

<210> SEQ ID NO 15
<211> LENGTH: 18
<212> TYPE: DNA
<213> ORGANISM: Artificial Sequence
<220> FEATURE:
<223> OTHER INFORMATION: Synthetic primer

<400> SEQUENCE: 15
aacgctagct acaggctt                                                     18

<210> SEQ ID NO 16
<211> LENGTH: 18
<212> TYPE: DNA
<213> ORGANISM: Artificial Sequence
<220> FEATURE:
<223> OTHER INFORMATION: Synthetic primer

<400> SEQUENCE: 16
caatcggagt tcttcgtg                                                     18

<210> SEQ ID NO 17
<211> LENGTH: 19
<212> TYPE: DNA
<213> ORGANISM: Artificial Sequence
<220> FEATURE:
<223> OTHER INFORMATION: Synthetic primer

<400> SEQUENCE: 17
tccgtaggtg aacctgcgg                                                    19

<210> SEQ ID NO 18
<211> LENGTH: 20
<212> TYPE: DNA
<213> ORGANISM: Artificial Sequence
<220> FEATURE:
<223> OTHER INFORMATION: Synthetic primer

<400> SEQUENCE: 18
ttggtccgtg tttcaagacg                                                   20

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
gcatatcaat aagcggagga                                          20

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
tccctttcaa caatttcacg                                          20

<210> SEQ ID NO 21
<211> LENGTH: 22
<212> TYPE: DNA
<213> ORGANISM: Artificial Sequence
<220> FEATURE:
<223> OTHER INFORMATION: Synthetic primer

<400> SEQUENCE: 21
ttaggcctta gcgggcttag ac                                       22

<210> SEQ ID NO 22
<211> LENGTH: 22
<212> TYPE: DNA
<213> ORGANISM: Artificial Sequence
<220> FEATURE:
<223> OTHER INFORMATION: Synthetic primer

<400> SEQUENCE: 22
ccaggatttt tgatgggaca cg                                       22

<210> SEQ ID NO 23
<211> LENGTH: 28
<212> TYPE: DNA
<213> ORGANISM: Artificial Sequence
<220> FEATURE:
<223> OTHER INFORMATION: Synthetic primer

<400> SEQUENCE: 23
aagagcacca aggatgacca gcaatgtc                                 28

<210> SEQ ID NO 24
<211> LENGTH: 24
<212> TYPE: DNA
<213> ORGANISM: Artificial Sequence
<220> FEATURE:
<223> OTHER INFORMATION: Synthetic primer

<400> SEQUENCE: 24
aggagaaggc agcacaggca ctag                                     24

<210> SEQ ID NO 25
<211> LENGTH: 28
<212> TYPE: DNA
<213> ORGANISM: Artificial Sequence
<220> FEATURE:

```
<223> OTHER INFORMATION: Synthetic primer

<400> SEQUENCE: 25
gcgcccgaga atcacttggt ttcacatt                                          28

<210> SEQ ID NO 26
<211> LENGTH: 28
<212> TYPE: DNA
<213> ORGANISM: Artificial Sequence
<220> FEATURE:
<223> OTHER INFORMATION: Synthetic primer

<400> SEQUENCE: 26
ggagcagaga cagagcgacc catacctg                                          28
```